(12) United States Patent
Kim et al.

(10) Patent No.: US 7,466,063 B2
(45) Date of Patent: Dec. 16, 2008

(54) MICRO MANIPULATOR FOR MOVEMENT OF ELECTRODE, DRIVING METHOD THEREOF, AND MEASURING DEVICE OF BRAIN SIGNAL USING THE SAME

(75) Inventors: Byung-kyu Kim, Seoul (KR); Suk-ho Park, Seoul (KR); Hee-sup Shin, Gyeonggi-do (KR); Dae-soo Kim, Daejeon (KR); Hyun-jun Park, Seoul (KR); Jong-oh Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 395 days.

(21) Appl. No.: 11/475,177

(22) Filed: Jun. 27, 2006

(65) Prior Publication Data

US 2007/0296310 A1    Dec. 27, 2007

(51) Int. Cl.
     *H01L 41/053*     (2006.01)
     *H01L 41/08*      (2006.01)
     *H02N 2/02*      (2006.01)

(52) U.S. Cl. .............................. 310/323.17; 310/323.01; 310/328; 310/367; 310/368; 310/369; 600/378; 606/129; 606/130

(58) Field of Classification Search ............ 310/323.01, 310/323.17, 328, 363–366; 600/378; 606/129–130
See application file for complete search history.

(56) References Cited

U.S. PATENT DOCUMENTS

| | | | | |
|---|---|---|---|---|
| 4,724,351 A | * | 2/1988 | EerNisse et al. | ............ 310/328 |
| 4,998,938 A | * | 3/1991 | Ghajar et al. | ................ 606/130 |
| 5,237,238 A | * | 8/1993 | Berghaus et al. | ............ 310/328 |
| 6,267,770 B1 | * | 7/2001 | Truwit | ......................... 606/130 |
| 6,380,661 B1 | * | 4/2002 | Henderson et al. | ...... 310/323.02 |
| 6,836,056 B2 | * | 12/2004 | Oudshoorn et al. | ......... 310/328 |
| 7,141,914 B2 | * | 11/2006 | Kallio et al. | ........... 310/323.17 |
| 2007/0228868 A1 | * | 10/2007 | Park et al. | .................... 310/300 |

* cited by examiner

*Primary Examiner*—Jaydi SanMartin
(74) *Attorney, Agent, or Firm*—McDermott Will & Emery LLP (57) ABSTRACT

A micro manipulator for electrode movement, a driving method thereof, and a brain signal measuring device using the same are provided. The micro manipulator has a guide member having a rectangular hollow hole therein, first and second piezo-electric clamp bodies installed perpendicular to the movement direction of the electrode between the inner opposite sides in the hollow hole of the guide member such that respective both ends thereof are selectively fixed to or separated from the inner sides of the hollow hole depending upon whether of the application of electric power thereto, a drive piezo-electric body whose both ends are connected to the opposite faces, respectively, of the first and second clamp piezo-electric bodies to selectively expand or contract in parallel with the movement direction of the electrode depending upon whether of the application of electric power thereto, and an electrode holder holding therein the electrode and installed on the first or second clamp piezo-electric body in parallel with the expansion or contraction direction of the drive piezo-electric body.

4 Claims, 11 Drawing Sheets

FIG. 1

(Prior Art)

FIG. 2

(Prior Art)

|   | FIRST CLAMP PIEZO-ELECTRIC BODY | SECOND CLAMP PIEZO-ELECTRIC BODY | DRIVE PIEZO-ELECTRIC BODY |
|---|---|---|---|
| 1 | ON | ON | OFF |
| 2 | OFF | ON | OFF |
| 3 | OFF | ON | ON |
| 4 | ON | ON | ON |
| 5 | ON | OFF | ON |
| 6 | ON | OFF | OFF |

MICRO MANIPULATOR FOR MOVEMENT OF ELECTRODE, DRIVING METHOD THEREOF, AND MEASURING DEVICE OF BRAIN SIGNAL USING THE SAME

BACKGROUND OF THE INVENTION

1. Field of the Invention

The present invention relates to a micro manipulator for moving an electrode, a driving method thereof, and a measuring device of a brain signal using the same, and more particularly to a micro manipulator capable of moving an electrode to a desired position through the more precise movement of the electrode approaching the cranial nerve cells, a driving method thereof, and a measuring device of a brain signal using the same.

2. Description of the Prior Art

Typically, there are approximately $10^{11}$ neurons in a brain of a human being, and the neurons transfer information by means of electric signals. For the analysis of a function of the neuron, there have been proposed analysis methods for analyzing an electrical characteristic of the brain neuron for an external stimulus, and a vital reaction under an electrical stimulus for specified brain neuron.

Figure 1:
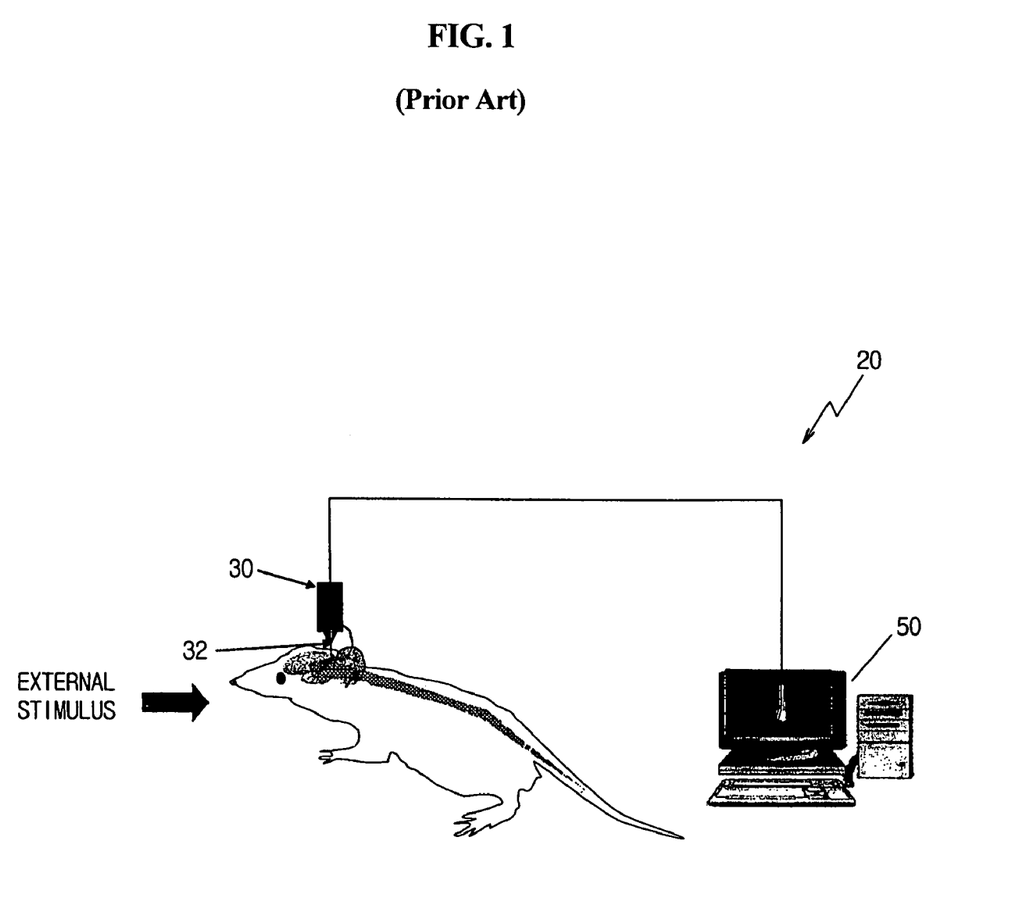
FIG. 1 is a schematic concept diagram illustrating a conventional brain signal measuring device.

A conventional measuring device for measuring a brain signal of the brain neurons is shown in FIG. 1. The conventional brain signal measuring device includes an electrode 32 for detecting an electric signal of the brain neurons or applying an electric signal to the brain neurons, a micro-manipulator 30 for moving the electrode 32 nearer to or away from the brain neurons, and a signal processor 50 for amplifying an electric signal from the electrode 32, converting the amplified signal into a digital signal, and analyzing the digital signal.

Figure 2:
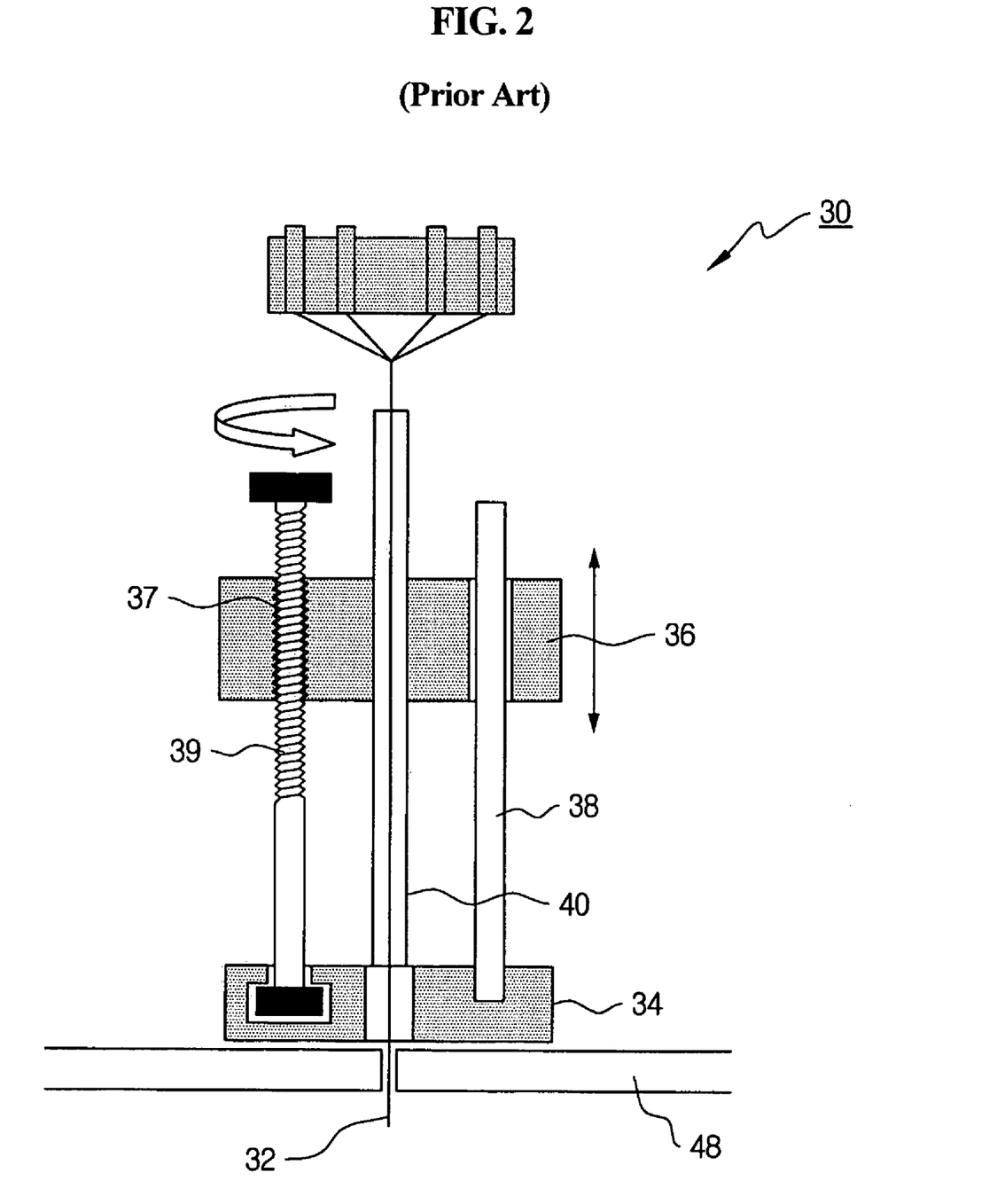
FIG. 2 is a schematic view illustrating a construction of a conventional micro manipulator.

FIG. 2 is a schematic view illustrating a construction of a conventional micro manipulator 30. In FIG. 2, the conventional micro manipulator 30 includes a lower support 34 fixed to the upper portion of a skull 48, a drive shaft 39 and a guide bar installed perpendicular to the lower support 34, an upper support 36 moving vertically along the guide bar 38 by the drive shaft 39, an electrode holder 40 fixedly installed to the upper support 36 to pass through the lower support 334, and an electrode 32 fixedly inserted into the electrode holder 40.

The drive shaft 39 is rotatably installed on the lower support 34 and whose outer surface is threaded. In addition, the upper support 36 has therein a drive hole 37 through which the drive shaft 39 passes and whose inner wall is threaded, so that the upper support 36 moves upward or downward (vertically in FIG. 2) along the guide bar 38 according to a rotation direction of the drive shaft 39.

Together with the upward or downward movement of the upper support 36, the electrode 32 held in the electrode holder 40 installed on the upper support 36 also moves upward or downward. Accordingly, an operator rotates the drive shaft 39 to move the electrode 32 nearer to or away from the brain neurons (not shown) in the skull 48. In this case, a capability to move the electrode 32 to a desired position from the brain neurons is called a distance resolution.

In the conventional manipulator 30, the movement of the upper support 36 and the electrode 32 is regulated by the adjustment of a pitch of screw reads and a rotation angle of the drive shaft 39. Thus, in the conventional micro manipulator, with all precise manufacturing of the drive shaft, there is a limit to accurately regulate the electrode, so that the distance resolution is considerably reduced, causing a problem in that it is difficult to accurately position the electrode to a desired position from the brain neurons.

SUMMARY OF THE INVENTION

Accordingly, the present invention has been made to solve the above-mentioned problems occurring in the prior art, and an object of the present invention is to provide a micro manipulator for movement of an electrode capable of precisely positioning the electrode to a desired position from the brain neurons through the improvement of a distance resolution of the electrode approaching the brain neurons, a driving method thereof, and a brain signal measuring device using the same.

In order to accomplish the above object, there is provided a micro manipulator of a brain signal measuring device for moving an electrode for detecting an electric signal of the brain neurons or applying an electric signal to the brain neurons, the micro manipulator comprising: a guide member having a rectangular hollow hole therein; first and second piezo-electric clamp bodies installed perpendicular to the movement direction of the electrode between the inner opposite sides in the hollow hole of the guide member such that upon the supply of electric power, the clamp bodies expand in such a way that the respective both ends thereof bring in close contact with and are fixed to the inner sides of the hollow hole, and upon the cut off of electric power, the clamp bodies contract in such a way that the respective both ends thereof are separated from the inner sides of the hollow hole; a drive piezo-electric body whose both ends are connected to the opposite faces, respectively, of the first and second clamp piezo-electric bodies to selectively expand or contract in parallel with the movement direction of the electrode depending upon whether of the application of electric power thereto; and an electrode holder holding therein the electrode and installed on the first or second clamp piezo-electric body in parallel with the expansion or contraction direction of the drive piezo-electric body.

Herein, the guide member may have, at the opposite sides thereof parallel with the movement direction of the electrode, through-holes through which the electrode holder is installed to thus move just along the movement direction of the electrode.

In accordance with another aspect of the present invention, there is provided a method for driving a micro manipulator for movement of an electrode, the method comprising the steps of: applying electric power to first and second clamp piezo-electric bodies and cutting off electric power applied to a drive piezo-electric body to expand the first and second clamp piezo-electric bodies, thereby bringing the respective both ends of the first and second clamp piezo-electric bodies in close contact with the inner opposite sides of a guide member to fix the first and second clamp piezo-electric bodies thereto; cutting off electric power applied to the first clamp piezo-electric body to contract the same, thereby separating both ends of the first clamp piezo-electric body from the inner sides of the guide member; applying electric power to the drive piezo-electric body to expand the same in parallel with the movement direction of the electrode, thereby moving the first clamp piezo-electric body; applying electric power to the first clamp piezo-electric body to expand the same, thereby bring both ends of the first clamp piezo-electric body in close contact with the inner opposite sides of the guide member to fix the first clamp piezo-electric body thereto; cutting off electric power applied to the second clamp piezo-electric body to contract the same, thereby separating both ends of the second clamp piezo-electric body from the inner opposite sides of the guide member; and cutting off electric power applied to the drive piezo-electric body to contract the same in parallel with the movement direction of the electrode, thereby moving the second clamp piezo-electric body.

In accordance with still another aspect of the present invention, there is provided a wireless brain signal measuring device comprising: a micro manipulator; a controller for the control of the driving of the micro manipulator; a signal amplifier for the amplification of the signal from an electrode of the micro manipulator; and a radio frequency (RF) transmitter for the RF-transmission of the signal amplified by the amplifier.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, preferred embodiments of the present invention will be described with reference to the accompanying drawings.

Figure 3:
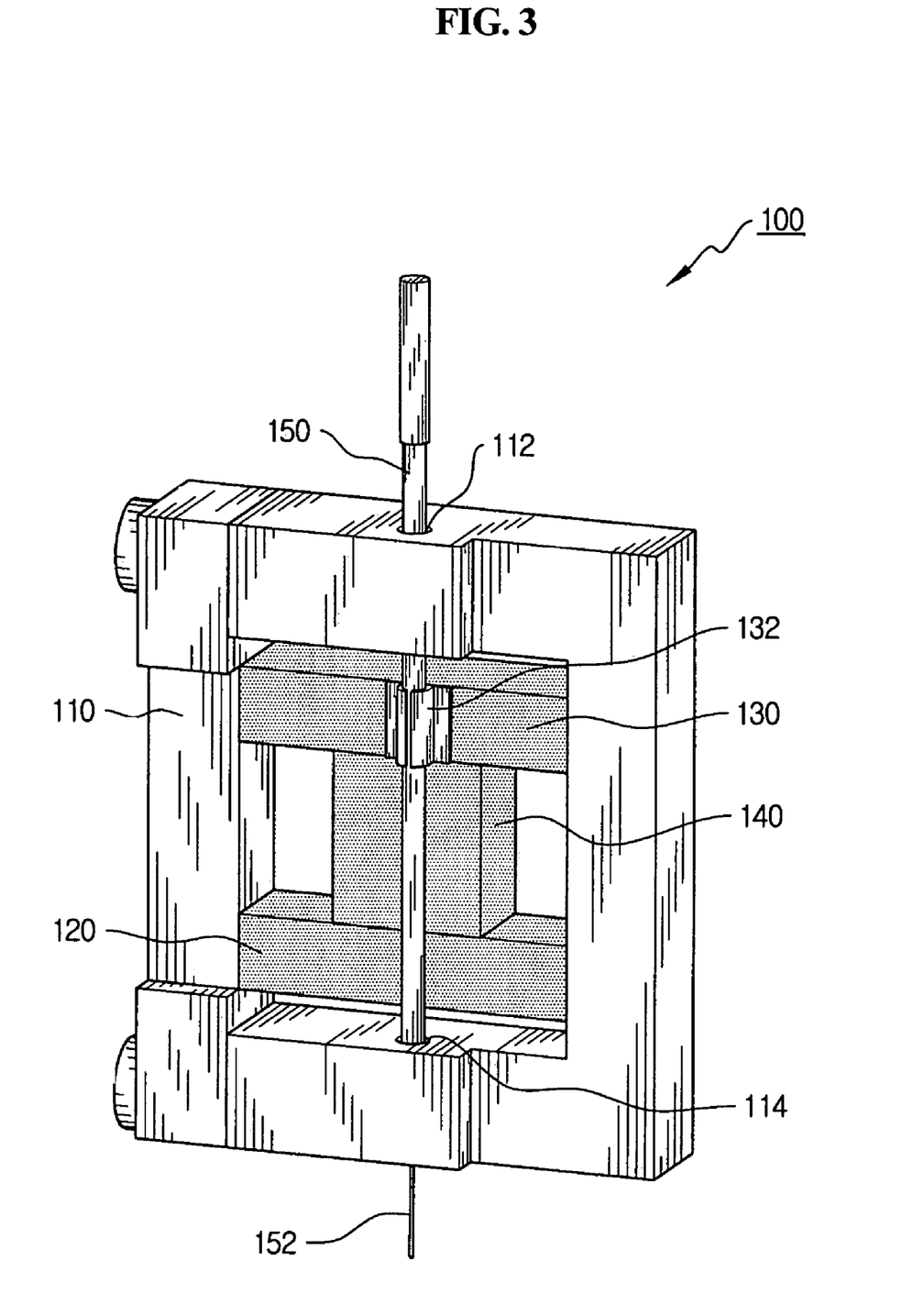
FIG. 3 is a perspective view of a micro manipulator for the movement of an electrode according to a preferred embodiment of the present invention.

FIG. 3 is a perspective view of a micro manipulator 100 for the movement of an electrode according to a preferred embodiment of the present invention.

Referring to FIG. 3, the micro manipulator 100 for the movement of the electrode includes a guide member 110 having a rectangular hollow hole therein, first and second piezo-electric clamp bodies 120 and 130 installed perpendicular to the movement direction of the electrode 152 between the inner opposite sides in the hollow hole of the guide member 100, a drive piezo-electric body 140 whose both ends are connected to the opposite faces, respectively, of the first and second clamp piezo-electric bodies 120 and 130, and an electrode holder 150 holding therein the electrode 152 and installed on the first or second clamp piezo-electric body 120 or 130 in parallel with the drive piezo-electric body 140. Meanwhile, in the present invention, the first and second clamp piezo-electric bodies 120 and 130 and the drive piezo-electric body 140 are made of a material that expands physically when electric power is applied thereto, so that the respective piezo-electric bodies have a property wherein upon the application of electric power thereto, they expand, and upon the cut off of electric power, they contract.

The guide member 110 is made of proper material with suitable strength, and has therein a rectangular hollow hole in which the respective piezo-electric bodies as described later are disposed. The guide member 110 serves to guide the movement of the respective piezo-electric bodies using the rectangular hollow hole.

The first and second clamp piezo-electric bodies 120 and 130 and the drive piezo-electric body 140 are disposed in the guide member 110. In particular, the first and second clamp piezo-electric bodies 120 and 130 are disposed perpendicular to the predetermined movement direction of the electrode 152, i.e., horizontally in FIG. 3, between the inner opposite sides in the hollow hole of the guide member 110. As described before, the first and second clamp piezo-electric bodies 120 and 130 expand through the application of the power source, and contract through the cut off of the power source. Accordingly, upon the expansion through the application of power to the first and second clamp piezo-electric bodies 120 and 130, the both ends thereof bring in contact with the inner opposite sides of the guide member 110 to fix the clamp piezo-electric bodies thereto. On the contrary, upon the contraction through the cut off of power from the first and second clamp piezo-electric bodies 120 and 130, the both ends thereof move away and are separated from the inner sides of the guide member 110.

Figure 9:
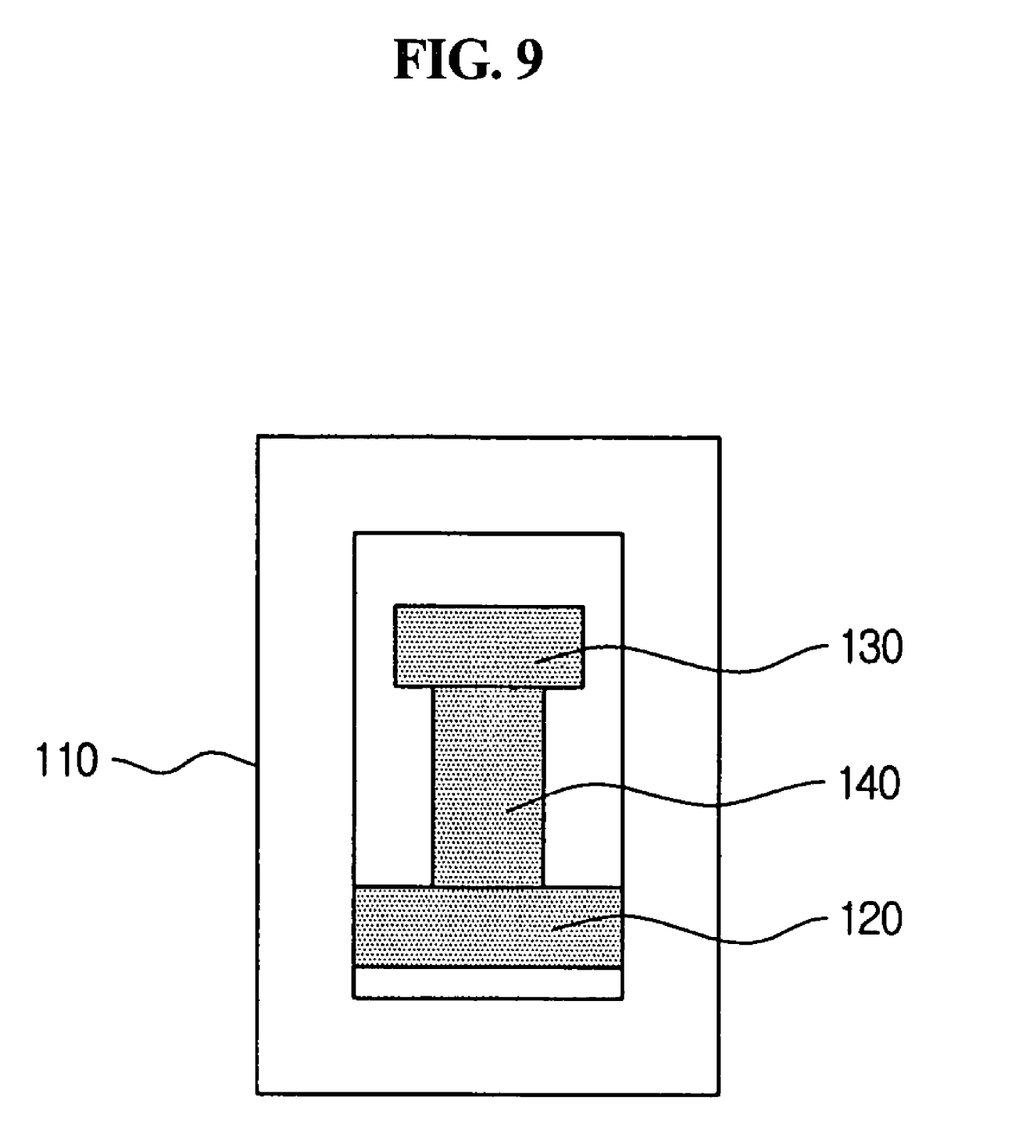

Meanwhile, the drive piezo-electric body 140, as shown in FIG. 3, is disposed in parallel with the predetermined movement direction of the electrode 152, i.e., perpendicular in FIG. 9, between the inner opposite faces of the first and second clamp piezo-electric bodies 120 and 130. Accordingly, upon the application of power to the drive piezo-electric body 140, the drive piezo-electric body 140 expands to move the first and second clamp piezo-electric bodies 120 and 130 installed at both ends thereof. A driving method according to the selective power application of the respective piezo-electric bodies will be described later in detail.

The electrode holder 150 is installed on the first or second clamp piezo-electric body 120 or 130 in order to hold and fix therein the electrode 152. In FIG. 3, although the electrode holder 150 has been illustrated as being fixedly installed on the second clamp piezo-electric body 130 by a fixture 132 for electrode holder, the position thereof is not limited thereto, but may be on the first clamp piezo-electric body 120. Since the electrode holder 150 is fixed onto the first or second piezo-electric body 120 or 130, the electrode holder 150 and the electrode 152 therein are moved together with the movement of the first or second piezo-electric body 120 or 130.

Meanwhile, through-holes 112 and 114 may be respectively formed on the inner opposite faces of the guide member 110 in parallel with the movement of the electrode 152. As the electrode 152 and the electrode holder 150 are moved through the through-holes 112 and 114, the electrode 152 and the electrode holder 150 can be moved accurately in a straight line without shaking.

Figure 4:
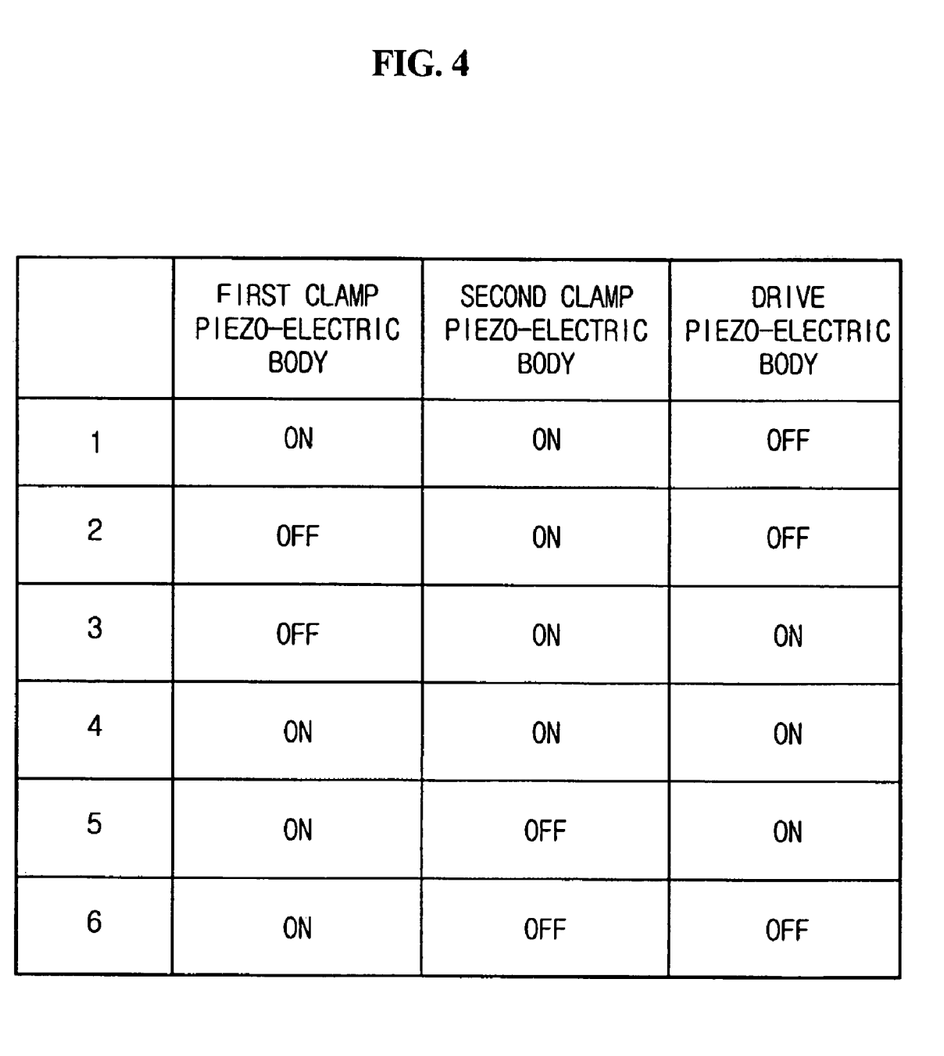
FIG. 4 is a table showing an order of applying electric power to the respective piezo-electric bodies in a driving method of a micro manipulator according to a preferred embodiment of the present invention.

A driving method for moving an electrode using the micro manipulator 100 having the above-mentioned construction according to a preferred embodiment of the present invention will now be explained with reference to the drawings. FIG. 4 is a table showing an order of applying an electric power to the first and second clamp piezo-electric bodies 120 and 130, and the drive piezo-electric body 140, and FIGS. 5 to 10 are views showing a drive order of the respective piezo-electric bodies according to the driving method of the micro manipulator of the present invention. FIG. 4 shows over whether or not to apply an electric power to the respective piezo-electric bodies at the corresponding steps. That is, 'on' indicates a state of application of power to the corresponding piezo-electric body, and 'off' indicates a state of cut off of power from the corresponding piezo-electric body. For example, at a step 1 in FIG. 4, the first and second clamp piezo-electric bodies 120 and 130 are applied with electric power, and the drive piezo-electric body 140 is in cut off state of electric power. Hereinafter, the driving method of the micro manipulator will be explained with reference to the drawings.

First, a main function of the micro manipulator is to move an electrode nearer to or away from the brain neurons. That is, the forward/backward movement of the electrode is the basic and essential function of the micro manipulator. In this context, the procedure of the movement of the electrode by the micro manipulator will now be explained. The basic operation principle of the micro manipulator is characterized in that an electric power is selectively applied to the three piezo-electric bodies to cause the piezo-electric bodies to contract and expand, thereby moving the electrode holder.

Figure 5:
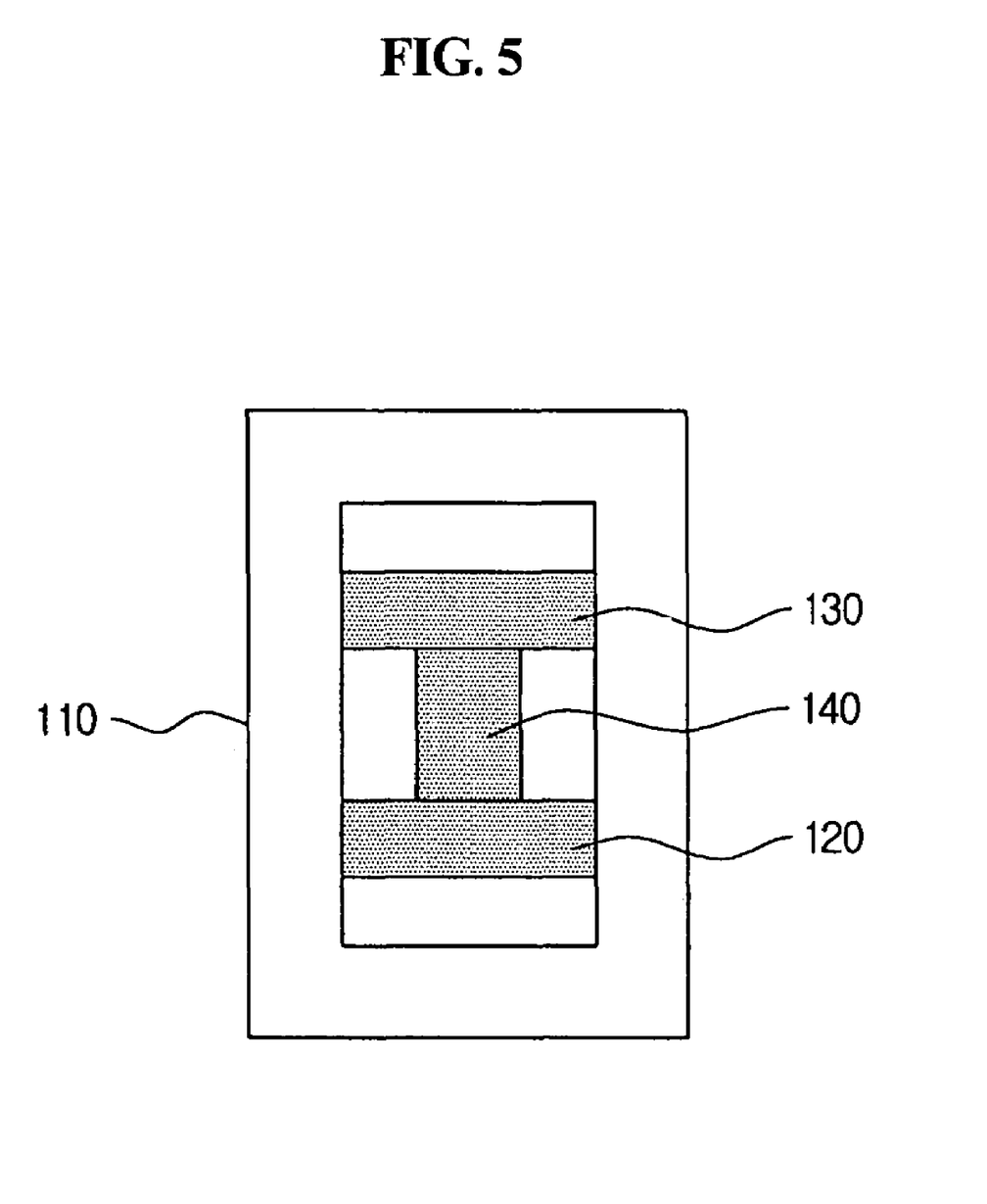
FIGS. 5 to 10 are views showing sequential driving states of the respective piezo-electric bodies in a driving method of a micro manipulator according to a preferred embodiment of the present invention.

In particular, at an initial state as shown in FIG. 5 corresponding to the step 1 of FIG. 4, among the three piezo-electric bodies 120, 130, and 140, the first and second clamp piezo-electric bodies 120 and 130 are applied with electric power, and the other drive piezo-electric body 140 is not applied with electric power. Accordingly, the first and second clamp piezo-electric bodies 120 and 130 expand such that the respective both ends thereof bring in contact with and are fixed to the inner opposite sides of the guide member 110. A term of clamp in the first and second clamp piezo-electric bodies 120 and 130 means that upon the application of electric power, the clamp piezo-electric bodies 120 and 130 are to be closely contacted with and fixed to the guide member 110.

Figure 6:
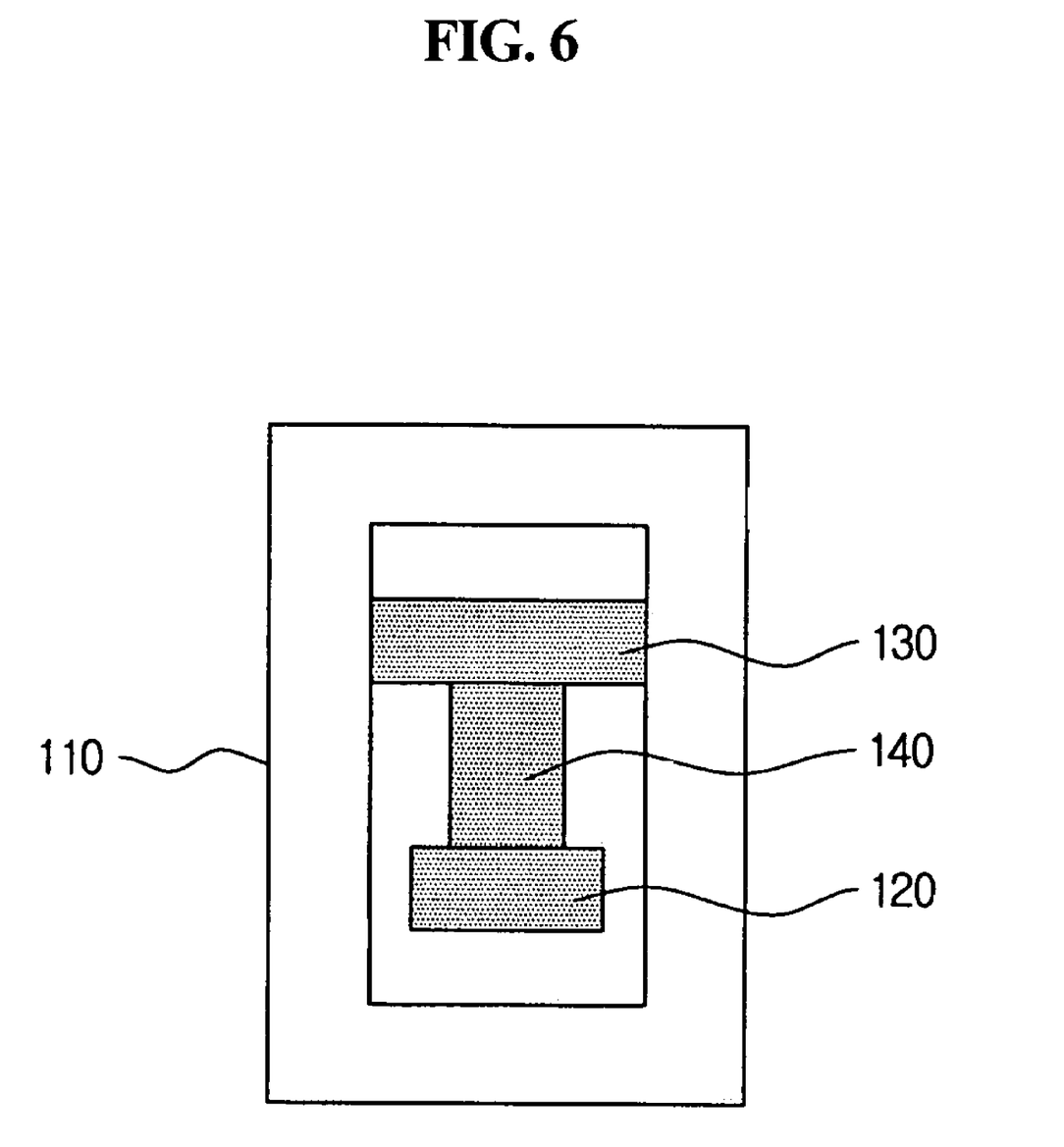

In this state, as shown in FIG. 6 corresponding to a step 2 of FIG. 4, if electric power applied to the first clamp piezo-electric body 120 is cut off, the first clamp piezo-electric body 120 contracts such that both ends thereof are released from a state of close contact and fixation to the guide member 110.

Figure 7:
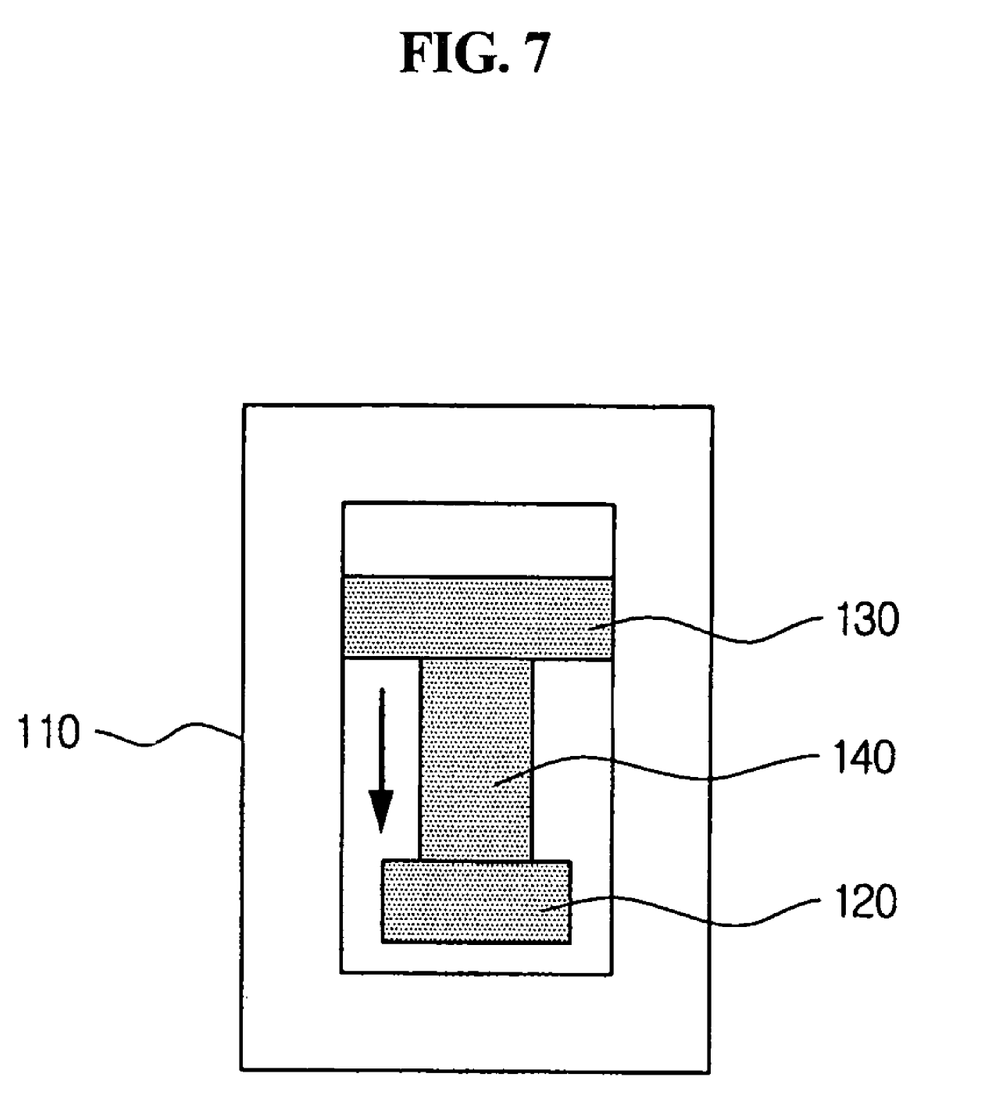

Then, as shown in FIG. 7 corresponding to a step 3 of FIG. 4, if electric power is applied to the drive piezo-electric body 140, the drive piezo-electric body 140 expands downward in an arrow direction in FIG. 7. In this case, since both ends of the first clamp piezo-electric body 120 are separated from the inner sides of the guide members 110, the first clamp piezo-electric body 120 moves downward in FIG. 7 as the drive piezo-electric body 140 expands.

Figure 8:
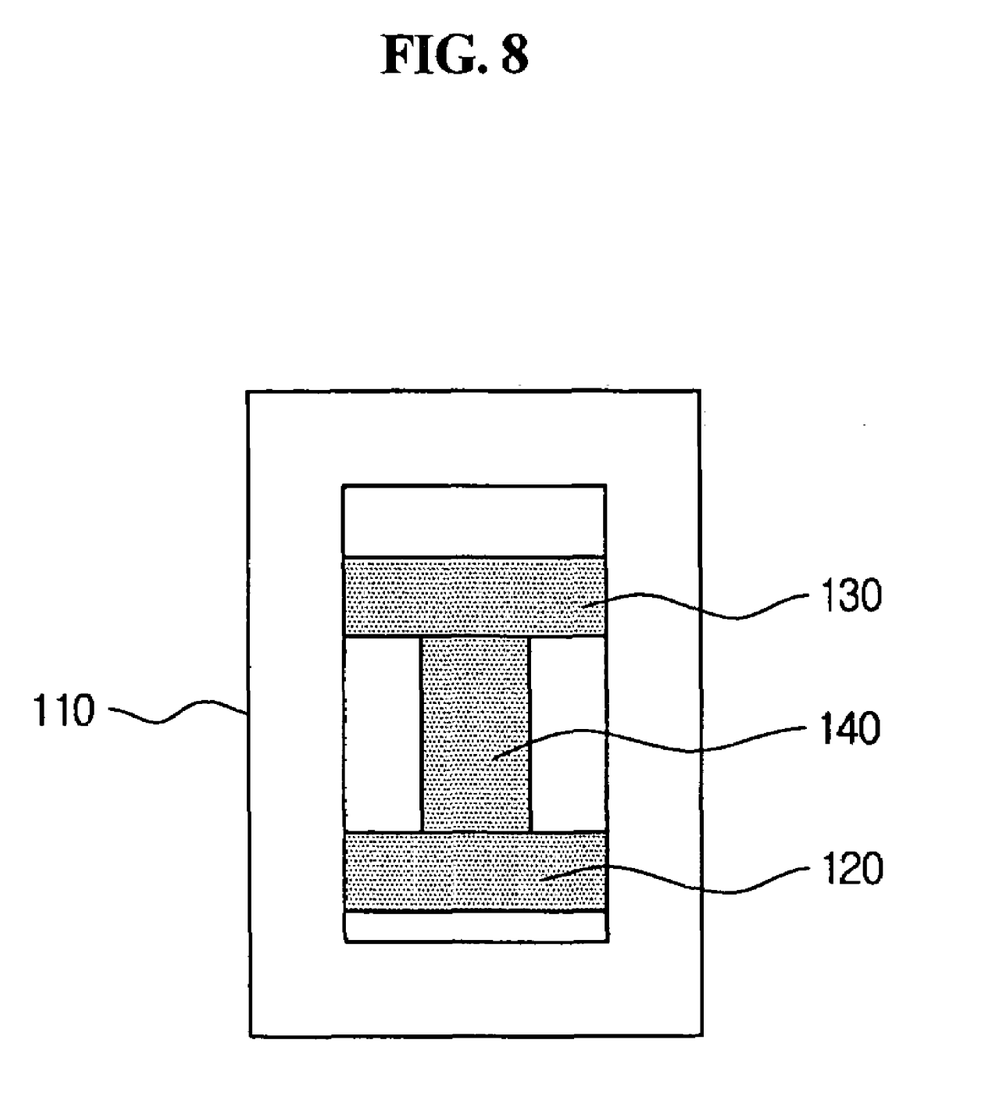

Then, as shown in FIG. 8 corresponding to a step 4 of FIG. 4, if electric power is applied again to the first clamp piezo-electric body 120, the first clamp piezo-electric body 120 expands such that both ends thereof bring in contact with and are fixed again to the inner sides of the guide member 110.

Next, as shown in FIG. 9 corresponding to a step 5 of FIG. 4, if electric power applied to the second clamp piezo-electric body 130 is cut off, the second clamp piezo-electric body 130 contracts such that both ends thereof are released from a state of close contact and fixation to the guide member 110.

Figure 10:
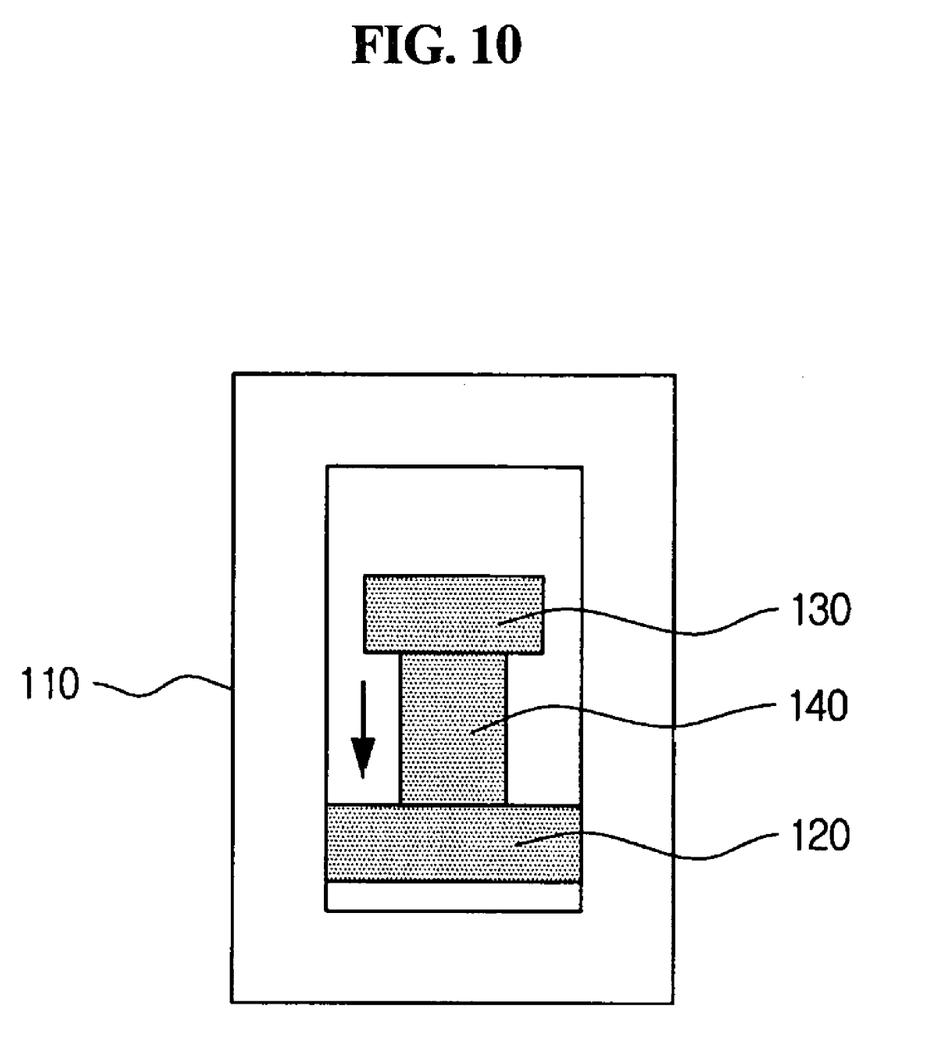

In the state where the second clamp piezo-electric body 130 is separated from the inner sides of the guide member 110, as shown in FIG. 10 corresponding to a step 6 of FIG. 4, if electric power applied to the drive piezo-electric body 140 is finally cut off, the drive piezo-electric body 140 contracts. Accordingly, the drive piezo-electric body 140 contracts downward in FIG. 10.

As shown in FIGS. 5 to 10, the electrode holder 150 (See FIG. 3) fixed to the upper portion of the first or second clamp piezo-electric body 120 or 130 and the electrode 152 held therein move to a distance, that is, an expansion distance of the drive piezo-electric body 140. The movement distance at this time is called a unit movement distance, i.e., a distance resolution. The unit movement distance, i.e., the distance resolution, is selectively changeable depending upon the composition material of polymer compounding the piezo-electric bodies, the magnitude of applied power, and others.

The unit movement distance, or the distance resolution of the micro manipulator 100 of the present invention can reach up to several tens to hundreds nm. FIGS. 5 to 10 have shown an operation of the downward movement of the electrode 152, and the upward movement of the electrode can be implemented through the inverse process of FIGS. 5 to 10.

In the mean time, in the micro manipulator of the present invention, since the three piezo-electric bodies are placed inside the guide member so that upon the application of voltage to the piezo-electric bodies, a minute mechanical force may be possibly exerted by the guide member, it is required a precise assembly between the three piezo-electric bodies and the guide member.

Figure 11:
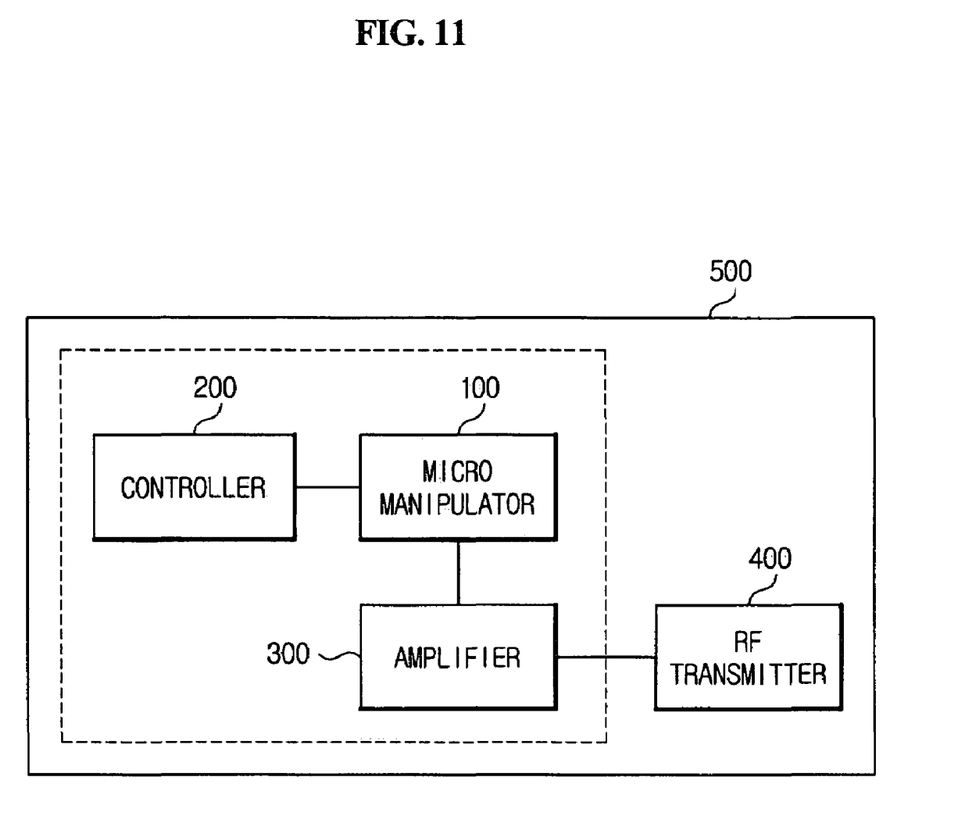
FIG. 11 is a block diagram of a brain signal measuring device including a micro manipulator for the movement of an electrode according to the present invention.

The above-mentioned micro manipulator for movement of the electrode and the driving method thereof of the present invention can be adapted to a wireless brain signal measuring device as shown in FIG. 11.

Referring to FIG. 11, the wireless brain signal measuring device 500 according to the present invention includes the micro manipulator 100 for movement of the electrode, a controller 200 for the control of the driving of the micro manipulator 100, an amplifier 300 for amplifying a signal from the electrode of the micro manipulator 100, and a radio frequency (RF) transmitter 400 for the RF-transmission of the signal amplified by the amplifier 300.

The controller 200 for the micro manipulator drives the micro manipulator 100 according to the driving method for the micro manipulator as described with reference to FIGS. 4 to 10, thereby positioning the electrode 152 (See FIG. 3) to a desired position. The construction of the micro manipulator 100 has been described in detail with reference to FIG. 3, so more detailed explanation thereof will be omitted.

The amplifier 300 amplifies a minute brain signal from the neurons through the electrode 152 to an extent of being made out. The amplifier 300 has insensitivity to external noise to solve a problem of being difficult to distinguish an original signal from noises generated in a transmission process, thereby allowing the more precise analysis of the brain signal.

The RF transmitter 400 transmits to an external measuring device the brain signal amplified by the amplifier 300, so that the brain signal can be measured in a wireless manner.

Meanwhile, the power source of the controller 200, the amplifier 300, and the RF transmitter 400 may be a battery or a wireless power transmission module (not shown). However, since the battery is hardly applied to active living organisms due to its weight and volume, the wireless power transmission module may be preferably used to overcome the defect.

As set forth above, the wireless brain signal measuring device can be applied to active living organisms, making it possible to measure the more various brain signals.

It is obvious that the brain signal measuring device using the micro manipulator can be embodied not only by a wireless manner, but also by a wire manner in which wire means transmits the brain signal without using the RF transmitter.

According to the present invention, a micro manipulator for movement of an electrode and a driving method thereof can considerably improve a distance resolution, i.e., capability to slightly move an electrode of a brain signal measuring device nearer to the brain neurons, using contraction and expansion features of a piezo-electric body causing mechanical deformation according to the application of power source.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A micro manipulator of a brain signal measuring device for moving an electrode for detecting an electric signal of the brain neurons or applying an electric signal to the brain neurons, the micro manipulator comprising:

a guide member having a rectangular hollow hole therein;

first and second piezo-electric clamp bodies installed perpendicular to the movement direction of the electrode between the inner opposite sides in the hollow hole of the guide member such that respective both ends thereof are selectively fixed to or separated from the inner sides of the hollow hole depending upon whether of the application of electric power thereto;

a drive piezo-electric body whose both ends are connected to the opposite faces, respectively, of the first and second clamp piezo-electric bodies to selectively expand or contract in parallel with the movement direction of the electrode depending upon whether of the application of electric power thereto; and an electrode holder holding therein the electrode and installed on the first or second clamp piezo-electric body in parallel with the expansion or contraction direction of the drive piezo-electric body.

2. The micro manipulator as claimed in claim 1, wherein the guide member has, at the opposite sides thereof parallel with the movement direction of the electrode, through-holes through which the electrode holder is installed.

3. A method for driving a micro manipulator as claimed in claim 1, the method comprising the steps of:

applying electric power to first and second clamp piezo-electric bodies and cutting off electric power applied to the drive piezo-electric body to expand the first and second clamp piezo-electric bodies, thereby bringing the respective both ends of the first and second clamp piezo-electric bodies in close contact with the inner opposite sides of the guide member to fix the first and second clamp piezo-electric bodies thereto;

cutting off electric power applied to the first clamp piezo-electric body to contract the same, thereby separating both ends of the first clamp piezo-electric body from the inner sides of the guide member;

applying electric power to the drive piezo-electric body to expand the same in parallel with the movement direction of the electrode, thereby moving the first clamp piezo-electric body;

applying electric power to the first clamp piezo-electric body to expand the same, thereby bring both ends of the first clamp piezo-electric body in close contact with the inner opposite sides of the guide member to fix the first clamp piezo-electric body thereto;

cutting off electric power applied to the second clamp piezo-electric body to contract the same, thereby separating both ends of the second clamp piezo-electric body from the inner opposite sides of the guide member; and cutting off electric power applied to the drive piezo-electric body to contract the same in parallel with the movement direction of the electrode, thereby moving the second clamp piezo-electric body.

4. A wireless brain signal measuring device comprising:

a micro manipulator as claimed in claim 1;

a controller for the control of the driving of the micro manipulator;

a signal amplifier for the amplification of the signal from the electrode of the micro manipulator; and a radio frequency (RF) transmitter for the RF-transmission of the signal amplified by the amplifier.

\* \* \* \* \*